(12) United States Patent
Imperial

(10) Patent No.: US 6,613,311 B2
(45) Date of Patent: Sep. 2, 2003

(54) SILICONE BASED HAIR BLEACH COMPOSITIONS AND RELATED METHODS

(75) Inventor: Teresita Vargaria Imperial, Staten Island, NY (US)

(73) Assignee: Revlon Consumer Products Corporation, New York, NY (US)

( * ) Notice: Subject to any disclaimer, the term of this patent is extended or adjusted under 35 U.S.C. 154(b) by 102 days.

(21) Appl. No.: 09/774,890

(22) Filed: Feb. 1, 2001

(65) Prior Publication Data

US 2002/0141954 A1 Oct. 3, 2002

(51) Int. Cl.[7] .................... A61K 7/135; A61K 7/06; A61K 7/13; A61K 7/07; C01B 15/017
(52) U.S. Cl. .................... 424/62; 424/401; 424/70; 424/70.11; 424/70.13; 424/DIG. 3; 424/70.24; 514/714; 514/880
(58) Field of Search ............... 424/62, 401, 70, 424/70.11, 70.13, DIG. 3, 70.24; 514/714, 880

(56) References Cited

U.S. PATENT DOCUMENTS

| | | | | |
|---|---|---|---|---|
| 5,851,544 A | * | 12/1998 | Penska et al. | 424/401 |
| 5,888,484 A | | 3/1999 | Schmitt | 424/62 |
| 5,891,423 A | * | 4/1999 | Weeks | 424/62 |

* cited by examiner

*Primary Examiner*—Frederick Krass
*Assistant Examiner*—Clinton Ostrup
(74) *Attorney, Agent, or Firm*—Julie Blackburn

(57) ABSTRACT

A composition for use in bleaching hair in combination with a liquid peroxide based oxidizing agent, said composition comprising an effective amount of at least one persulfate salt dispersed in a silicone oil base and a method for bleaching hair with said composition.

20 Claims, No Drawings

SILICONE BASED HAIR BLEACH COMPOSITIONS AND RELATED METHODS

TECHNICAL FIELD

The invention is in the field of persulfate and peroxide based compositions for bleaching hair.

BACKGROUND OF THE INVENTION

Hair bleaching is generally accomplished by mixing powdered persulfate salts with an alkalizing agent, together with an aqueous solution of oxidizing agent such as hydrogen peroxide and applying the mixture to the hair for an appropriate period of time. The hydrogen peroxide activates the persulfate salts and the mixture causes hair to decolorize, or lighten the melanin in the hair. Hair bleaching is particularly popular with individuals who have dark hair and wish to lighten it to the ever-popular blonde color or create highlights. Bleaching is also used when it is desired to dye hair in a color that is substantially lighter than the natural shade in a two step process. The bleach will lighten the hair and the subsequently applied hair dye will then color the fibers in the desired shade.

Traditional bleaching methods have a number of drawbacks. First, the persulfates used in the bleaching process are in fine particulate form and very susceptible to dusting. Due to the caustic nature of the alkalizing agent with the persulfate salts, this tendency to dusting causes certain problems in manufacturing as well as for the consumers who use the bleach. Another problem encountered in the bleaching process results from the tendency of the persulfate particles and other active ingredients to disperse unevenly during storage. As a result, some consumers will receive products with variable concentrations of active ingredients. Further, such compositions are very sensitive to proper mixing. Some consumers will mix the ingredients better than others and well mixed compositions will provide more consistent results than compositions that are not well mixed. Unfortunately, consumers do not always follow directions, which causes the mixture applied to hair to have varying persulfate concentrations over the area upon which it is placed. This, in turn, can cause the consumer to leave the bleach on the hair longer. Due to the possibility that bleaches can cause some weakening of the hair, it is most desirable to have bleaches that provide the desired color as quickly as possible.

It is well know that persulfate particles can be treated with a variety of agents to reduce dusting. Waxes and mineral oil are some of the ingredients which may be mixed with the particules to reduce dusting by causing particle agglomeration. The larger agglomerated particles are less likely to become airborne. However, these treatments do not address the problems with inconsistency in bleaching times and results.

U.S. Pat. No. 5,888,484 teaches persulfate compositions for bleaching hair which are in the paste form. The persulfates are combined with organic oils and waxes to form a paste composition. The paste composition is then combined with a peroxide based oxidizing agent to form a composition for bleaching the hair. However, the organic oils present do not seem to help in dispersing the persulfate particles evenly throughout the paste, nor do they appear to have any impact on reducing the time required to achieve coloration of the hair.

Accordingly, there is a need for a persulfate based composition that causes improved consistency in bleaching results, improved dispersion of persulfate particles in the mixture, and reduces the time in which bleaching occurs.

SUMMARY OF THE INVENTION

The invention is directed to a silicone based persulfate composition for use in bleaching hair in combination with an aqueous peroxide based oxidizing agent. The persulfate composition comprises an effective amount of at least one alkali metal salt persulfate in a silicone oil base. The persulfate composition is preferably in the form of a semi-solid or cream. The persulfate particles are well dispersed in the silicone oil, which tends to wet out the particles and cause them to better dissolve in the aqueous based peroxide oxidizing composition when the persulfate composition is mixed with the aqueous based oxidizing agent composition immediately prior to use.

The invention further comprises a method for bleaching the hair comprising applying to the hair a mixture of a composition comprised of a dispersion of alkali metal salt persulfate particles in a silicone oil base, and a liquid peroxide based composition, to the hair for a period of time sufficient to bleach the hair. The dispersion of the persulfate particles in the silicone oil base causes the mixture to be very homogeneous in consistency both before and after it is combined with the aqueous based peroxide composition. This results in a bleaching process that is very consistent. Moreover, the amount of time to achieve bleaching is reduced.

It is an object of the invention to provide a hair bleaching composition containing persulfate particles dispersed in an inert medium that will not react with the persulfate particles and at the same time will combine with the aqueous based peroxide composition immediately prior to use to form an emulsion that colors the hair in a reduced amount of time.

It is a further object of the invention to provide a semi-solid or cream hair bleaching composition containing persulfate particles dispersed in a silicone oil base which, when combined with an aqueous based peroxide composition and used to bleach hair, reduces the normal bleaching time by 20 to 40%.

It is a further object of the invention to provide semi-solid or cream hair bleaching composition for use in bleaching hair in combination with an aqueous based oxidizing agent, wherein when the two compositions are mixed, a water and silicone oil emulsion is obtained.

It is a further object of the invention to provide a method for bleaching hair comprising combining a semi-solid or cream composition containing persulfate particles dispersed in a silicone oil phase and an aqueous based peroxide composition and applying the mixture to the hair for a time sufficient to cause the hair to become bleached.

DETAILED DESCRIPTION

I. The Composition

The composition of the invention is preferably in the semi-solid or cream form and is used for bleaching hair in combination with a liquid peroxide based oxidizing agent. The term "semi-solid" or "cream" means that the composition is in the form of a cream or paste having a viscosity ranging from about 25,000 to 2,000,000 centipoise at 25° C.

The composition comprises an effective amount of at least one alkali metal salt persulfate dispersed in a silicone oil base. The composition is substantially free of water, meaning that it contains less than 5% by weight, preferably less than 1% by weight of water. The most preferred compositions are anhydrous.

A. The Alkali Metal or Ammonium Persulfate Salts

The claimed compositions comprise 10–90%, preferably 15–85%, more preferably 20–75% by weight of the total composition of one or more persulfate salts. Suitable persulfate salts include ammonium persulfate salts or alkali metal salt persulfates including but not limited to sodium persulfate, potassium persulfate, lithium persulfate, ammonium persulfate, and the like. Particularly preferred are sodium persulfate and potassium persulfate.

B. Silicone Oil

The claimed compositions comprise 10–90%, preferably 15–85%, more preferably 20–75% by weight of the total composition of a silicone oil base. The silicone oil base may be comprised of one or a mixture of two or more silicones. Preferably the silicone oil is a liquid at room temperature and may be volatile or nonvolatile. The term "volatile" means the silicone has a vapor pressure of at least 2 mm. of mercury at 20° C. The term "nonvolatile" means that the silicone has a vapor pressure of less than 2 mm. of mercury at 20° C.

1. Volatile Silicones

Suitable volatile silicones include cyclic silicones (or cyclomethicones) which are of the general formula:

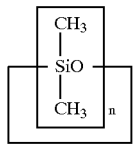

where n=3–6.

Linear volatile silicones in accordance with the invention have the general formula:

where n=0–6, preferably 0–5.

Linear and cyclic volatile silicones are available from various commercial sources including Dow Corning Corporation and General Electric. The Dow Corning volatile silicones are sold under the tradenames Dow Corning 244, 245, 344, and 200 fluids. These fluids comprise octamethylcyclotetrasiloxane, decamethylcyclopentasiloxane, hexamethyldisiloxane, and mixtures thereof.

3. Nonvolatile Silicones

Suitable nonvolatile silicones include water insoluble silicones having a viscosity of 10 to 600,000 centistokes, preferably 20 to 100,000 centistokes at 25° C. Suitable water insoluble silicones include dimethicone; $C_{6-30}$ alkyl dimethicones such as cetyl dimethicone; phenyl substituted silicones such as phenyl trimethicone, phenyldimethicone, diphenyl dimethicone; dimethicone copolyol, $C_{6-30}$ alkyl dimethicone copolyols, and mixtures thereof Such silicones are available from Dow Corning as the 3225C formulation aid, Dow 190 and 193 fluids, or similar products marketed by Goldschmidt under the ABIL tradename.

Also suitable as the nonvolatile silicone oil are various fluorinated silicones such as trimethylsilyl endcapped fluorosilicone oil, polytrifluoropropylmethylsiloxanes, and similar silicones such as those disclosed in U.S. Pat. No. 5,118,496 which is hereby incorporated by reference.

Preferably the claimed composition comprises the nonvolatile silicone dimethicone, more particularly dimethicone having a viscosity ranging from 50 to 500 centistokes at 25° C.

C. Other Ingredients

The claimed composition may contain additional ingredients that enhance the aesthetic and other desirable properties thereof, including but not limited to pH adjusters, hydrophilic thickeners, chelating agents, humectants, and the like.

1. pH Adjusters

Preferred compositions comprise 0.1–50%, preferably 1–45%, more preferably 5–40% by weight of the total composition of one or more pH adjusters. The term "pH adjuster" means an ingredient that is capable of changing the pH of the composition, preferably changing the pH by causing an increase in alkalinity. In bleaching compositions it is necessary to maintain adequate alkalinity so that when the persulfate composition is mixed with the liquid peroxide composition, the alkaline pH is maintained. Particularly preferred pH adjusters are particulates such as metallic silicates, e.g. sodium silicate, potassium silicate, magnesium silicate, sodium metasilicate, and so on. Particularly preferred is a sodium silicate.

2. Hydrophilic Thickening Agents

The claimed compositions preferably contain a hydrophilic thickener, which is hydrophilic material that is capable of adhering to the particulate materials in the composition. Further, when the persulfate composition is mixed with the aqueous based peroxide composition immediately prior to use, the hydrophilic thickener will thicken the aqueous portion of the composition so that the mixture will not drip as readily from the hair. Preferred amounts of hydrophilic thickener range from about 0.1–10%, preferably 0.5–8%, more preferably 1–7% by weight of the total persulfate composition. Suitable hydrophilic thickeners are carbohydrates, more particularly polysaccharides or polysaccharide derivatives which may be in the gum or particulate form. The term "gum" means that the carbohydrate has the ability to swell in water and increase the viscosity of aqueous preparations. A number of carbohydrate gums are suitable for use in the claimed compositions, such as xanthan gum, dextran, guar, gellan gum gelatin, guar hydroxyethyl cellulose, guar hydroxypropyl cellulose, cellulose, pectin, and the like. Particularly preferred is xanthan gum.

3. Absorbents

The preferred bleach compositions according to the invention additionally comprise one or more absorbents which are generally particulates having a larger surface area which can attract dissolved or finely dispersed substances from another medium. In particular, the absorbents will improve the stability of the persulfate based composition by reducing the tendency of the particulates to separate out from the silicone oil.

Suggested ranges of absorbent are 0.01–20%, preferably 0.05–10%, more preferably 1–8% by weight of the total composition. Examples of suitable absorbents include aluminum silicate, oat bran, oat kernel flour, oat kernel meal, oat starch, bentonite, calamine, calcium silicate, chalk, orange peel powder, corn starch, diatomaceous earth, corn starch, rice starch, fuller's earth, talc, zeolite, kaolin, hectorite, aluminum starch octenylsuccinate, silica, nylon, and the like. Particularly preferred is aluminum starch octenylsuccinate.

4. Chelating Agents

Preferably, the claimed compositions contain one or more chelating agents which act to bind metal ions found in water after the bleach composition is mixed with the aqueous peroxide composition. Suggested ranges of chelating agent are 0.01–10%, preferably 0.5–8%, more preferably 1–7% by weight of the total composition. A variety of chelating agents are suitable such as EDTA, HEDTA, TEA-EDTA, sodium metaphosphate, sodium metasilicate, and so on. Particularly preferred is EDTA.

II. The Method

The invention further comprises a method for bleaching the hair comprising applying to the hair a mixture of a composition comprised of a dispersion of persulfate salt particles in a silicone oil base, and a liquid peroxide based composition, to the hair for a period of time sufficient to bleach the hair.

Generally, the persulfate composition is combined with an aqueous peroxide based composition in a ratio of 1–10 parts of persulfate composition to 10–1 parts of aqueous peroxide based composition. More preferably, the ratio of the persulfate based composition and aqueous based peroxide composition is about 1 to 1.

Suitable peroxide based compositions generally comprise a peroxide based oxidizing agent in water. Suitable peroxides include hydrogen peroxide and organic peroxides. A variety of aqueous based peroxide compositions are suitable. Generally such compositions comprise 1–50% of the peroxide, and 1–50% water. The peroxide compositions may contain one or more additional ingredients such as surfactants, emollients, humectants, and the like.

The persulfate bleach composition and aqueous peroxide composition are mixed together immediately prior to use and applied to the hair for a time sufficient to cause bleaching of the hair. Generally bleaching is accomplished in 30 to 45 minutes, however it may be desirable to leave the mixture on the hair for 5 to 60 minutes depending on the effect desired. Thereafter, the composition is rinsed from the hair with water. If desired the hair may be treated with a hair conditioning composition.

The invention will be further described in connection with the following examples which are set forth for the purposes of illustration only.

EXAMPLE 1

A silicone based persulfate composition was made according to the following formula:

|  | w/w % |
| --- | --- |
| Potassium persulfate | 30.00 |
| Sodium silicate | 30.00 |
| EDTA | 1.00 |
| Xanthan gum | 3.95 |
| Dimethicone (350 centistokes) | 30.00 |
| Aluminum starch octenylsuccinate | 5.00 |
| Ultramarine blue | 0.05 |

The composition was made by combining the powdered ingredients and mixing well to disperse. The dry mixture was combined with dimethicone and mixed well. The result was a medium blue colored semi-solid composition that was stored in a glass container.

EXAMPLE 2

The composition of Example 1 was used to bleach blond hair by combining about 43 grams of the Example 1 composition with 43 grams of a 20 volume hydrogen peroxide solution and mixing well. The composition was applied to hair for 20 minutes, and then rinsed off. The hair exhibited significant lightening, even after 20 minutes which is substantially less time than required by normal bleaching processes.

I claim:

1. An anhydrous semi-solid paste or cream composition for use in bleaching hair in combination with a liquid peroxide based oxidizing agent, said composition comprising an effective amount of at least persulfate salt dispersed in a silicone oil base.

2. The composition of claim 1 which is a semi-solid paste.

3. The composition of claim 1 which comprises 1–90% by weight of the total composition of at least one persulfate salt which is an alkali metal persulfate salt or an ammonium persulfate salt.

4. The composition of claim 3 comprising 1–90% by weight of the total composition of silicone oil.

5. The composition of claim 4 wherein the silicone oil is a volatile silicone or a nonvolatile silicone.

6. The composition of claim 5 wherein the silicone oil has a viscosity of 0.5 to 1,000,000 centistokes at 25° C.

7. The composition of claim 6 wherein the silicone oil has a viscosity of 5 to 500,000 centistokes at 25° C.

8. The composition of claim 7 wherein the silicone oil is dimethicone.

9. The composition of claim 1 wherein the persulfate salt is sodium persulfate, potassium persulfate, or mixtures thereof.

10. The composition of claim 1 further comprising 0.1–50% by weight of the total composition of a pH adjuster.

11. The composition of claim 10 wherein the pH adjuster is a particulate metallic silicate.

12. The composition of claim 11 wherein the metallic silicate is sodium silicate.

13. The composition of claim 1 further comprising 0.1–10% by weight of the total composition of a hydrophilic thickener.

14. The composition of claim 13 wherein the hydrophilic thickener is a polysaccharide.

15. The composition of claim 14 wherein the polysaccharide is xanthan gum.

16. The composition of claim 14 wherein the polysaccharide derivative is aluminum starch octenylsuccinate.

17. The composition of claim 1 further comprising 0.01–5% by weight of the total composition of a chelating agent.

18. A method for bleaching the hair comprising applying to the hair a mixture of an anhydrous semi-solid paste or cream composition comprised of a dispersion of persulfate salt particles in a silicone oil base, and a liquid peroxide based composition, to the hair for a period of time sufficient to bleach the hair.

19. The method of claim 18 wherein the composition is in the semi-solid paste form and comprises 10–90% by weight of the total composition of persulfate salt and 10–90% by weight of the total composition of silicone oil.

20. The method of claim 19 wherein the liquid peroxide based composition comprises hydrogen peroxide and water in a ratio of 15 to 35 parts hydrogen peroxide and 65 to 85 parts water.

* * * * *